United States Patent [19]
Maitz et al.

[11] Patent Number: 5,098,418
[45] Date of Patent: Mar. 24, 1992

[54] ASPIRATOR DEVICE FOR BODY FLUIDS

[76] Inventors: Carlos A. Maitz, 16451 Dapple Gray Ct., Chesterfield, Mo. 63017; George R. Hauser, 29 Chieftan Dr., St. Louis, Mo. 63146

[21] Appl. No.: 570,795

[22] Filed: Aug. 22, 1990

Related U.S. Application Data

[63] Continuation-in-part of Ser. No. 398,098, Aug. 24, 1989, abandoned.

[51] Int. Cl.⁵ .................. A61M 1/00; A61M 37/00; A61M 1/06
[52] U.S. Cl. .................. 604/319; 604/323; 604/141; 604/73
[58] Field of Search ........... 604/319, 321, 315, 75, 604/73, 317, 318, 320, 323, 324, 141, 144

[56] References Cited

U.S. PATENT DOCUMENTS

| | | | |
|---|---|---|---|
| 3,911,920 | 10/1975 | Susinn | 604/78 |
| 4,643,719 | 2/1987 | Garth et al. | 604/315 |
| 4,799,925 | 1/1989 | Rosenblatt | 604/319 |

*Primary Examiner*—Ronald Frinks
*Assistant Examiner*—R. Clarke
*Attorney, Agent, or Firm*—Polster, Lieder, Woodruff & Lucchesi

[57] ABSTRACT

An aspirator, a suction device for removing body fluids, is disclosed. It includes two elongated tubes: one having a tapered end for insertion into body cavities via the nose or mouth for communication with body fluids; the other elongated tube having a mouthpiece, for mouth actuation, or a squeeze-bulb, for hand actuation. The free ends of the aforementioned elongated tubes are connected to a combination isolation and liquid-collection chamber. The chamber includes an elastic impregnable barrier against the transfer of potentially infective agents between patient and user. The chamber is constructed for venting gas and vapor components from the body fluid, as well as collecting the liquid component. For mouth actuation, the user holds the mouthpiece between his or her teeth while inserting the tapered end into the body cavity from which fluid is to be extracted. The user then seals his or her lips about the mouthpiece and alternately decreases and increases the volume of his or her mouth cavity as many times as required to extract the fluid sought. During hand operation, the user grips a squeeze-bulb in one hand and squeezes and releases same as many times as necessary to remove the sought after liquid.

20 Claims, 6 Drawing Sheets

ASPIRATOR DEVICE FOR BODY FLUIDS

CROSS REFERENCE TO RELATED APPLICATION

This application is a continuation-in-part of our earlier filed co-pending parent application Ser. No. 07/398,098 filed Aug. 24, 1989, now abandoned.

BACKGROUND OF THE INVENTION

This invention relates to an aspirator device for removing body fluids, and more particularly, to an aspirator device which allows fluid to be withdrawn from a patient's body cavity without contact with the user of the aspirator device.

Aspirator devices are used to remove meconium and other body fluids from newborn infants during and after the delivery process. An obstetrician typically utilizes the aspirator device during the delivery process. Pediatricians also use the aspirator to remove fluids from a newborn infant following delivery.

One aspirator device that is typically used for this purpose is the "De Lee Suction Catheter With Mucus Trap" manufactured by the Sherwood Medical Company of St. Louis, Miss. This device includes two elongated flexible plastic tubes each having one end connected to a mucus trap or liquid collector. The free end of one of the elongated flexible-plastic tubes forms a catheter-type tip for insertion into the mouth of a newborn infant, while the free end of the other elongated flexible plastic tube includes a mouthpiece for mouth actuated operation by a physician. When a physician inserts the catheter-type tip into an infant's body cavity, via the infants mouth, and sucks on the mouth-piece in the aspirator device, body fluids are drawn from the baby, even while the newborn infant is still in the birth canal. Fluids, including both gas and vapors as well as liquids, which often contains suspended-particulate matter, are drawn from the body cavity. The gas and vapor components of body fluid are drawn into the user's mouth and the liquid component is collected in the mucus trap. The gas and vapor components drawn into the user's mouth are thereafter ejected into the atmosphere. On occasion, where there is an excessive amount of meconium in the body cavity, or the mucus trap becomes inadvertently tipped or tilted from the vertical, meconium fluid can be drawn into the mouth of a physician. While this unpleasant circumstance does not repeatedly occur, every obstetrician and pediatrician has faced this situation. If the baby or the mother is infected with Aids and/or other highly contagious disease, it is apparent that the continued use of such aspirator devices is not desirable.

Another disadvantage of current aspirator devices is that they use long and thin catheters which impose high drag to the flow of liquids of even moderate viscosity requiring an unnecessarily greater effort by the user when drawing fluid from a body cavity.

Some hospitals recommend against using the aforementioned commonly used aspirator device or require that it be connected to a remote vacuum pump as the suction source. Such vacuum sources are not always available, and when they are, they impose certain inconveniences such as connecting a hose between the aspirator and vacuum pump, and regulating the vacuum. Aspirators designed for use with remote-vacuum sources are equipped with vented-coupling adapters. For the user to draw fluid from a patient he or she must cover the vent with one of the fingers of one hand while manipulating the catheter into and within the body cavity from which fluid is to be drawn with the other hand thereby requiring two hands to operate the aspirator when one hand is needed to steady and guide the newborn through the birth. Alternatively an assistant can be used to make and break the vacuum on command from the user. In addition, there is always a chance of contaminating the entire hospital vacuum system. The aspirator disclosed herein is not limited to the delivery room of well equipped hospitals. It can be used in doctors offices and elsewhere where vacuum sources are not generally available. An example of such a use is the removal of fluid from nasal sinuses.

In an attempt to alleviate the potential for spread of disease associated with the aforementioned typically used aspirator device, some manufactures have inserted filters between the mouthpiece and the mucus trap or fluid collector of the aspirator device seeking to catch ultra-microscopic and sub-microscopic organisms and infectious agents. It is well known that filtering devices that pass the flow of gas easily by themselves are incapable of completely filtering-out all minute-harmful organisms or agents. In addition, such filters have been known to block flow through the aspirator device as a result of latent-minute liquid droplets carried to the filter by gas drawn through the filter from the infant's body cavity and by the liquid meconium coming into contact with the filter. When blockage occurs, the physician may have to discard the entire aspirator device and then retrieve a new one in order to continue the removal of meconium or other fluids from the newborn infant.

In order to allow a physician or other user to both remove and measure the quantity of meconium from a newborn infant, while also permitting excess overflowing fluids to be removed from the system, without risk to the user, we have disclosed a new and improved apparatus and method in our prior co-pending application Ser. No. 07/144,375 which was filed on Jan. 5, 1988 and entitled "ASPIRATOR DEVICE FOR BODY FLUIDS", now U.S. Pat. No. 4,921,488 dated May 1, 1990. In our aforementioned patent, we have employed a squeeze bulb which is operatively associated with first and second one-way valves which open in the same direction, the first valve establishing a vacuum in the system for removing and depositing potentially harmful liquids in the mucus trap or liquid collector, and the second valve not only working to establish the vacuum, but also serving as an overflow valve for the gas and vapor component of body fluids as well as any liquid component that exceeds the capacity of the liquid-collector. The squeeze bulb is operatively associated relative to the other components of the aspirator device to also facilitate one-handed gripping, lifting and operation of the aspirator device by the squeeze bulb.

While our aforementioned patent demonstrates a novel and unique apparatus and method for overcoming the aforenoted deficiencies of prior art devices, we have discovered still another way of achieving the same end result.

As is well known, present mouth-actuated aspirator devices have several very desirable features including suspension of the aspirator device from the user's mouth, often prior to the emergence of the infant's head, thus freeing the user's hands to manipulate the infant though the birth canal, or facilitating the holding of the infant's head with one hand, while guiding the catheter through the infant's mouth or nose into the body cavity with the other. Also, it is well known that current mouth-actuated aspirators are low cost, disposable, sanitary devices which have a very high degree of reliability from physical failure.

The present invention is directed primarily to a mouth-operated aspirator which overcomes all of the aforenoted deficiencies, while retaining the above recited advantages which are inherent in mouth-actuated aspirator devices. It will also be seen in the discussion that is to follow that the novel and unique apparatus of the present invention may also be used as a hand operated aspirator device.

SUMMARY OF THE INVENTION

Among the several objectives and advantages of the present invention may be noted:

The provision of a new and improved aspirator device for removing body fluids from a body cavity which retains all of the advantages of prior art devices, without any of the aforementioned deficiencies;

The provision of a new and improved aspirator device which allows removal of the components of body fluids from a body cavity, without permitting any of the components of body fluid to be ingested into the user's mouth;

The provision of a new and improved mouth-operated aspirator device which allows the user's mouth to serve as the actuating-pumping source for the aspirator device, without allowing any fluid components to be drawn into the user's mouth;

The provision of the aforementioned mouth-operated or hand-operated aspirator device which includes an elastic and impregnable barrier that expands or contracts in response to changes in volume of the user's mouth cavity to remove body fluids from a body cavity, while separating the user from contact with such body fluids;

The provision of the aforementioned aspirator device which includes a combination isolation and liquid-collection chamber (also called isolation chamber) in which the impregnable barrier operates, while permitting liquids to be collected in the isolation and liquid-collection chamber for measurement purposes and analysis;

The provision of the aforementioned aspirator device which facilitates suitable venting and one-way flow of gas, vapor or excess body liquids from the combination isolation and liquid-collection chamber; and The provision of the aforementioned aspirator device which reduces the level of suction required to remove body fluids by incorporation of a catheter tube which maintains a relatively large inside diameter from its origin inside the air-tight chamber to within a short distance from the distal end whereupon it tapers gradually to form a more flexible tip for insertion into body cavities.

The provision of the aforementioned aspirator device which is simple in construction, easy-to-operate and use, is economical to manufacture in large quantities; overcomes the major deficiency of prior art mouth-operated aspirator devices; has a high benefit-to-cost ratio; has a high physical reliability; and is otherwise well adapted for the purposes intended.

Briefly stated, the mouth-actuated aspirator for removing body fluids includes at least one elongated tube having one free end for insertion into a body cavity for fluid communication with body fluids and a second free end connected to a mouth piece for establishing a differential pressure in at least one elongated tube, a combination isolation and liquid-collection chamber associated with the at least elongated tube and including an inflatable/deflatable impregnable barrier in the isolation chamber which is inflated or deflated to provide differential pressure in at least the elongated tube to allow body fluids to be removed through the elongated tube for deposit in the isolation chamber, while separating the mouthpiece from the fluid flow in the elongated tube.

In a second embodiment, a hand-operated aspirator device uses a squeeze bulb as an air source in lieu of mouth operation.

Preferably, the at least one elongated tube includes a first elongated tube having one free end for insertion into a body cavity and a second end with a normally-closed one-way valve tip mounted within the isolation chamber and a second elongated tube having a mouth piece or squeeze bulb at one free end and having a second end disposed within the isolation chamber.

The inflatable/deflatable elastic barrier or booster is arranged to extend across the isolation chamber between the second ends of the first and second elongated tubes. The elastic barrier or booster may also include an elastic balloon barrier or booster which is connected to the mouth piece tube or squeeze bulb, as desired.

The aspirator device includes one-way venting means in the combination isolation and liquid-collection chamber to vent gas and vapor or excess body liquids therefrom. The one-way venting means includes a one-way exit tube having a normally closed one-way valve tip outside the isolation chamber and an open upper end within the isolation chamber which extends for a predetermined distance above the one-way valve tip of the first elongated tube within the isolation chamber in order to allow body liquids to be collected in the isolation chamber below the open-upper end of the one-way exit tube.

The isolation chamber is preferably a liquid collector having an upper transverse opening with the inflatable/deflatable elastic barrier being positioned across the upper transverse opening, and the top closure having a through opening for receiving the second elongated tube therein. Alternatively, the balloon barrier or booster may be connected to the second elongated tube within the chamber. The combination isolation and liquid-collector chamber also includes a lower transverse opening and a bottom closure for overlying and closing the lower transverse opening. Through openings are provided in the bottom closure for receiving the one-way exit tube and the first elongated tube therethrough.

These and other objectives and advantages of the present invention will become apparent from the description that is to follow.

BRIEF DESCRIPTION OF THE DRAWINGS

In the drawings.

Corresponding reference numerals will be used throughout the various figures of the drawings.

DESCRIPTION OF THE PREFERRED EMBODIMENT

The following detailed description illustrates the invention by way of example, and not by way of limitation. This description will clearly enable one skilled in the art to make and use the invention, and describes several embodiments, adaptions, variations, alternatives and uses of the invention, including what we presently believe is the best mode of carrying out the invention.

In the discussion that is to follow, the term "fluid" or "fluids" as used herein includes gases, vapors and liquids with or without suspended particulate solids, or any combination thereof.

Figure 1:
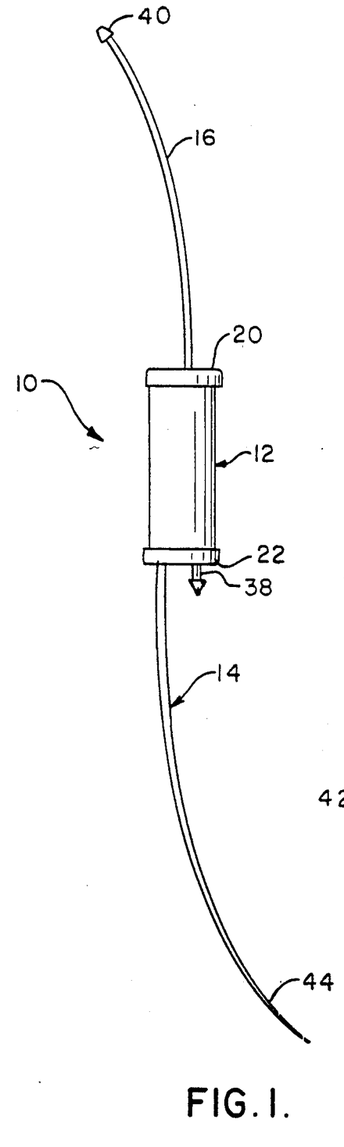
FIG. 1 is a reduced-in-size side elevational view of the mouth-operated aspirator device which is constructed in accordance with the teachings of the present invention.

As seen in FIG. 1 of the drawings, the aspirator device 10 includes an air-tight combination isolation and liquid-collector chamber 12 (also called isolation chamber) for receiving body fluids, a body catheter or first elongated tube 14 connected to one end of the isolation chamber 12, and a pump tube or second elongated tube 16 connected to the opposite end of the isolation chamber 12.

Figures 2, 3:
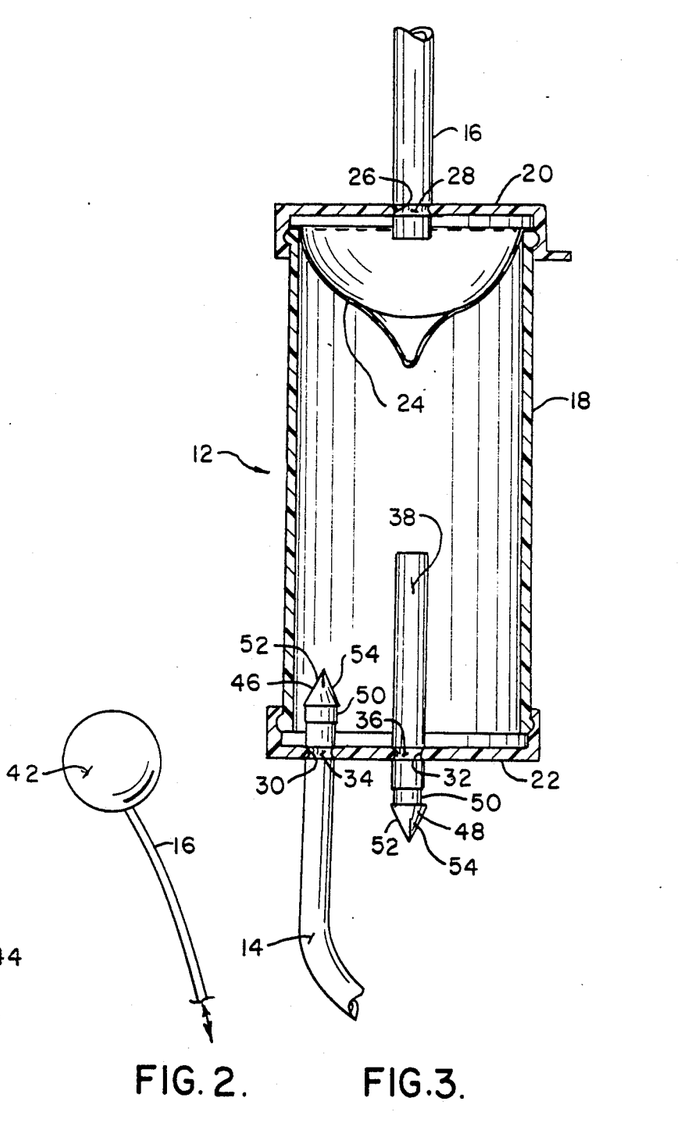
FIG. 2 is a fragmentary view illustrating the use of a squeeze bulb as a pumping air source, in lieu of the mouthpiece utilized in the FIG. 1 embodiment.
FIG. 3 is an enlarged sectional view of the combination isolation and liquid-collector chamber associated with the aspirator device of the present invention.

The combination isolation and liquid collection chamber 12, as best seen in FIG. 3, includes a right-circular cylinder 18, which is preferably molded from suitable clear-plastic material. Top and bottom closures or snap-on caps 20, 22 overlie and cover the open upper end and open bottom end of the cylinder 18 so as to provide an air tight isolation chamber and fluid collector therewithin. The isolation chamber 12 includes an inflatable/deflatable elastic impregnable barrier or booster 24 which extends across the open upper end of the cylinder 18 and is partially folded over the upper rim and downwardly along the outer cylindrical wall of the cylinder 18 for a short distance. The top closure or snap-on cap 20 is snapped into position over the barrier 24, including the top rim of the cylinder 18, in order to form an air-tight seal between the closure or cap 20, the impregnable barrier 24 and the cylinder 18. (A condom was used as the barrier 24 in certain experimental and prototype units.)

In a second configuration, the elastic barrier or booster 24 is inserted upwardly into the cylinder 18 a distance sufficient to loosely enclose the exit tube 38 and one-way valve 46 when the aspirator is fully assembled. The open end of the barrier is folded over the lower rim of the cylinder 18 and upwardly along the outer wall of the cylinder 18 for a short distance. The bottom closure or snap-on cap 22 is then placed over the barrier 24 and pressed to seal firmly and thereby form an air-tight seal between the barrier 24 and the cylinder 18.

The top closure or snap-on cap 20 has a through opening 26 for receiving the lower end of the pump tube 16, the tube 16 having a formed groove along the outside circumference of the tube which preferably has a root diameter larger than the through opening in the top closure or snap-on cap 20. When the tube 16 is assembled relative to the top closure or snap-on cap 20, the groove 28 will be readily received within the through opening 26 thereof so as to firmly meet and hold the pump tube 16 relative to the top closure or snap-on cap 20. For assembly purposes, the pump tube 16 and the top closure or snap-on cap 20 are first assembled to one another, and thereafter, the top closure or snap-on cap 20 is assembled relative to the cylinder 18 of the isolation chamber 12, in order to capture the outer peripheral areas of the elastic barrier relative to the cylinder 18, as described above.

The bottom closure or snap-on cap 22 includes two through openings 30, 32. One of the openings 30 receives and engages the groove 34 at an upper end of the body catheter 14 in air-tight sealed relationship. The other through opening 32 of the bottom closure or snap-on cap 22 engages a similar groove 36 formed adjacent the lower end of an exit tube 38 which extends for a substantial distance upwardly within the isolation chamber 12, but which also extends to the elastic barrier 24 when inflated, for purposes which will be described below.

The manner in which the pump tube 16, the body catheter 14 and the exit tube 38 are connected to the isolation chamber 12 in order to provide an air-tight seal may be varied to suit the particulars desired, with various types of interlocking sealed arrangements, as will be understood.

The pump tube 16, the body catheter 14 and the exit tube 38 are all preferably formed from suitably sized and dimensioned plastic material in an elongated hollow configuration, as is well known. Preferably, both the body catheter and pump tube elongated tubes 14, 16 are relatively flexible. The exit tube 38 may be constructed of the same material or of a material having greater rigidity, as will be further understood in the use and operation of the aspirator device 10 described below.

The pump tube 16 has a small mouthpiece 40 for reception within the mouth of a physician or other user. The mouthpiece is assembled to the pump tube by means of a tapered circular section that is pushed into tube 16 to provide a secure union of mouthpiece 40 and tube 16. The mouthpiece 40 enables the user to suspend the aspirator device 10 from the user's mouth, thus freeing the physician's hands for other purposes during the delivery process, as will be understood. In lieu of integrally formed hollow mouth piece 40 at the upper end of the pump tube 16, a squeeze bulb 42, as shown in FIG. 2, may be used, if desired. Since the squeeze bulb 42 will result in extra cost for the aspirator device 10, the preferable air source for the aspirator device 10 is the physician's or user's mouth. Therefore, the aspirator device 10, as disclosed in the FIG. 1 and 3-13 embodiment, is primarily a mouth-operated aspirator device 10.

The body catheter 14, as shown in FIG. 1, is a low drag catheter which maintains a relatively constant inside diameter for the greater portion of its length and then tapers downwardly to a lower diameter tip 44, in order to facilitate insertion of the body catheter 14 into a body cavity, such as an infant's body cavity entered via the mouth or nose. The upper end of the body catheter 14, as shown in FIG. 3, extends above the bottom closure or snap-on cap 22 a small distance and receives a normally-closed one-way tip or valve 46 which opens and closes in response to the presence of differential pressures between the inside and outside surfaces of the one-way tip or valve 46, as will be described below.

Similarly, the lower end of the exit tube 38 is also provided with a one-way tip or valve 48 which also opens and closes in response to the presence of differential pressure between the inside and outside surfaces of the one-way tip or valve 48.

Each of the normally-closed one-way tips or valves 46 and 48 are constructed of a soft resilient plastic material. They include a cylindrical section 52 which resiliently grip and seal the one-way tip or valves 46, 48 to the body catheter 14 and exit tube 38, respectively. Further, each of the one-way tips or valves 46 and 48 further include two flat sections, herein called walls 52, 54. The operation of the one-way tips or valves 46 and 48, including the walls 52, 54 thereof is best understood with reference to FIGS. 10-12 of the drawings. In each of FIGS. 10-12, the valve 46 is shown as being positioned within a closed environment such as the cylinder 58. Cylinder 58 is included only to facilitate this description. It is not a required part and is shown only in FIGS. 10-12 and was not used in prototype units. The one-way tip or valve 48 will operate in the identical manner as one-way tip 46.

Figure 10:
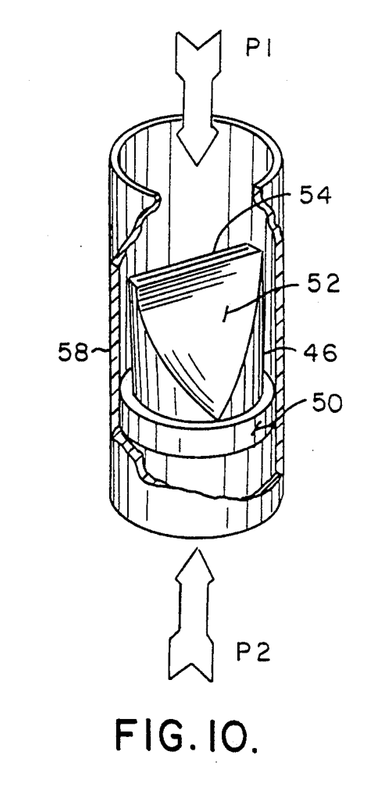
FIG. 10 is a fragmentary perspective view, partially in section, illustrating the normally-closed one-way valve or one-way tip utilized in the aspirator device of the present invention, and further showing the valve or tip being closed when the pressure on opposite sides thereof, namely P1 and P2, are equal.
Figure 11:
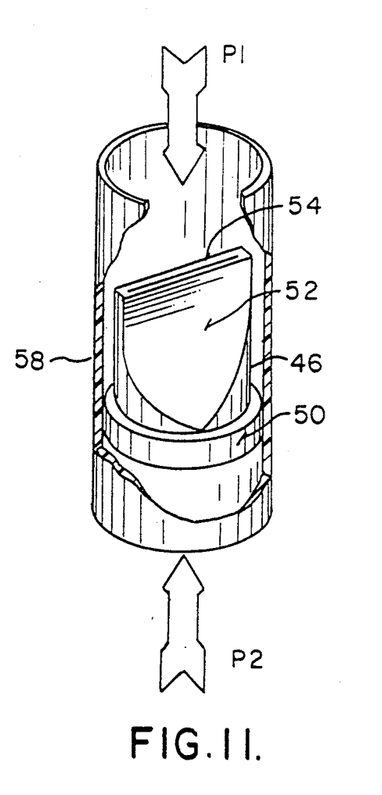
FIG. 11 is a view similar to FIG. 10 but showing the pressure P1 greater than the pressure P2 causing the valve or tip to be forced in an even more tightly closed condition.
Figure 12:
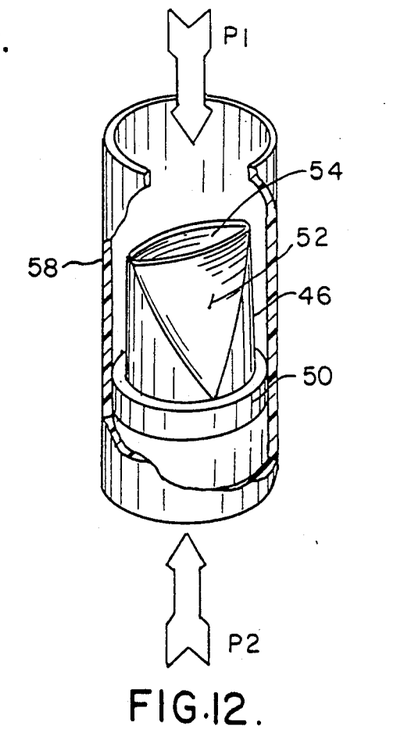
FIG. 12 is a view similar to FIGS. 10–11, and in this instance, the pressure P1 is less than the pressure P2, causing the valve or tip to open easily in order to permit fluid flow, as may be desired.

FIGS. 10-12 represent various pressure environments and uses to which the valve 46, for example, would be exposed. All one-way tips or valves are normally-closed one-way devices. In FIG. 10 of the drawings, the pressure P1 and pressure P2 are equal on the outside and inside surfaces, respectively, of the one-way tip or valve 46, and walls 52, 54 are closed to flow. When the pressure P1 on the outside surfaces of the one-way tip is greater than the pressure P2 on the inside surface of the one-way tip or valve 46, as shown in FIG. 11 of the drawings, the valve walls 52, 54 are forced even closer to one another so as to prevent the flow of fluid through the tip. When the pressure P1, on the outside surface, is less than the pressure P2, on the inside surfaces, of the valve 46, as shown in FIG. 12, the walls 52,, 54 are easily forced open, thus permitting fluid to flow through the one-way tip or valve 46 in the direction from P2 to P1.

Figure 4:
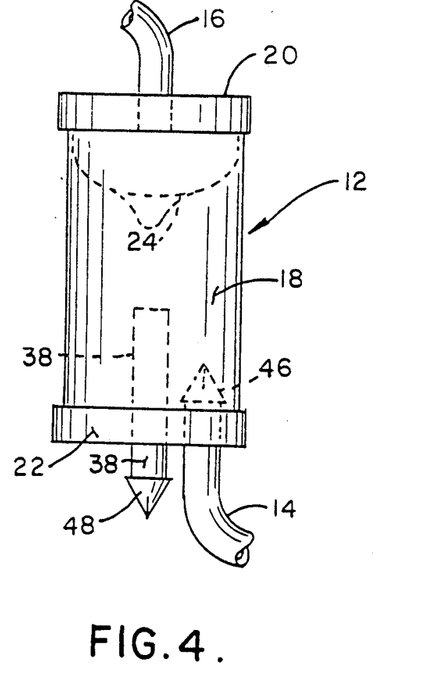
FIG. 4 is a fragmentary side elevational view of the combination isolation and liquid-collection chamber, including associated components, used in the aspirator device.
Figure 5:
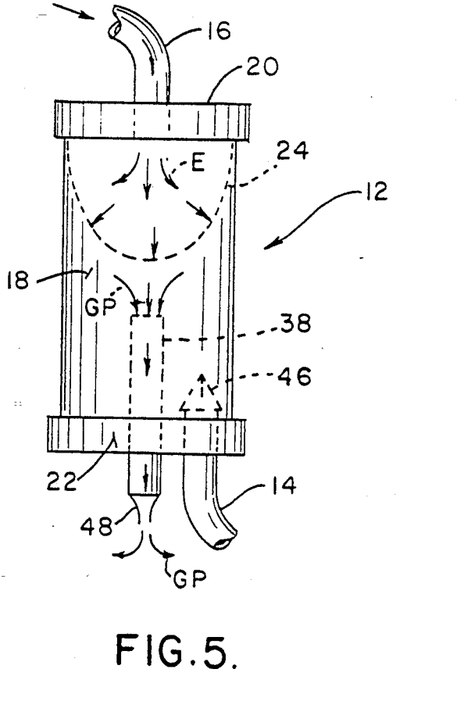
FIG. 5 is a fragmentary side elevational view similar to FIG. 4 and showing the manner in which the impregnable barrier within the isolation chamber or liquid-collection chamber is inflated, and further also showing the venting of gas and vapor and excess liquid from the combination isolation and liquid-collector chamber.
Figure 6:
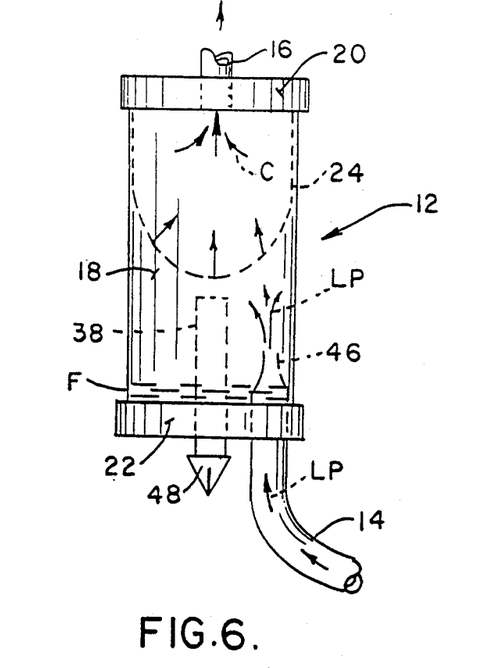
FIG. 6 is a view similar to FIGS. 4–5, but depicts the beginning of the deflation of the impregnable barrier in order to establish a negative air pressure to withdraw fluids from the body cavity for deposit in the combination isolation and liquid-collection chamber.
Figure 7:
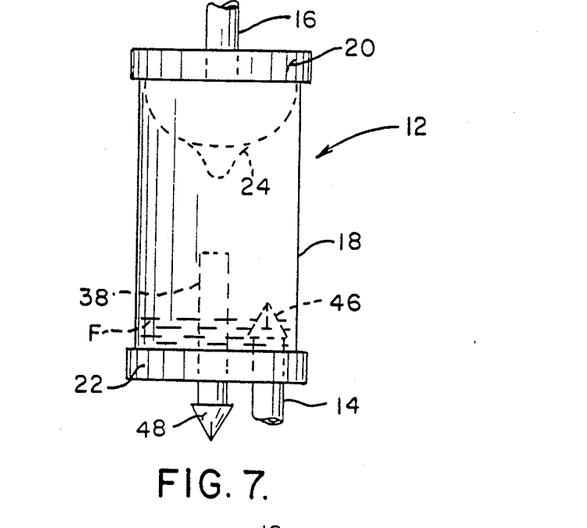
FIG. 7 is a view similar to FIGS. 4–6 and showing the combination isolation and liquid-collection chamber in a normal orientation for collection of liquids therein.
Figure 8:
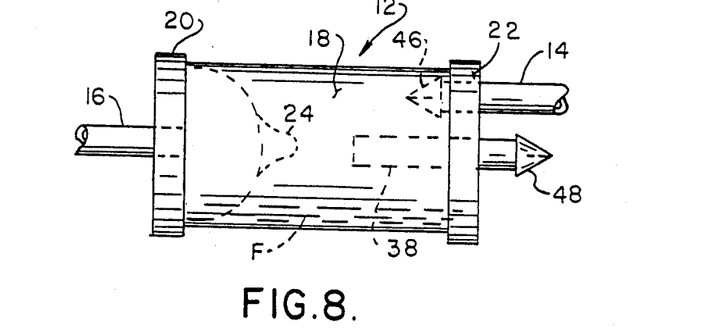
FIG. 8 is a view similar to FIGS. 4–7, but with the aspirator device in a tilted or tipped orientation, and illustrating the continuous operation of the aspirator device including a collection of liquids in the combination isolation and liquid-collection chamber.
Figure 9:
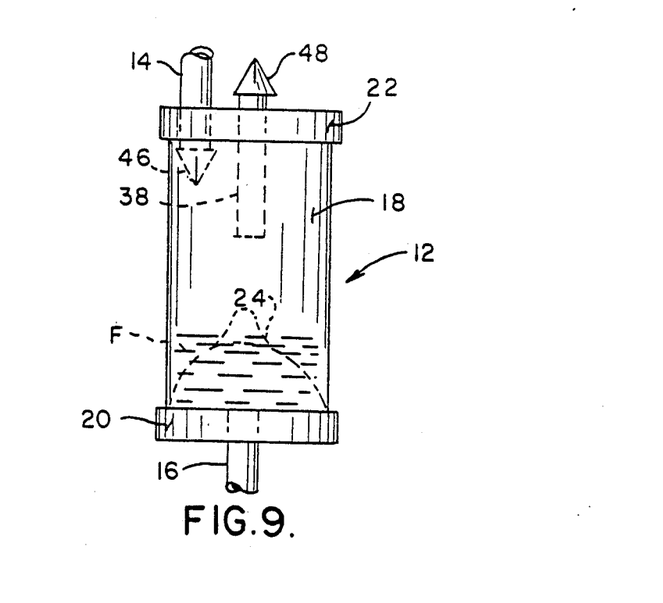
FIG. 9 is a view similar to FIGS. 4–8, but in this instance the combination isolation and liquid-collection chamber is in an upside-down or inverted orientation as compared with FIG. 7, with continued functioning and operation.

With the above explanation in mind, reference is now made to FIGS. 4-6 which illustrate the operation of the aspirator device 10 and FIGS. 7-9 which further illustrate operation of the aspirator device 10 in various degrees of attitude or orientation.

When the user is ready to extract body fluid from a body the user seals his or her lips about the mouthpiece 40 and decreases the volume of his or her mouth cavity causing the displaced air from his or her mouth to flow through the mouthpiece 40 and mouthpiece catheter 16 into the space between the top closure or snap-on cap 20 and the barrier 24. This air, from the user's mouth, inflates the barrier 24 and increases the volume between the top closure or snap-on cap 20 and the barrier 24. This increase in volume simultaneously causes a very slight pressure rise in the chamber 10 in the space bounded by the barrier 24, cylinder 18 and bottom closure or snap-on cap 22. This small rise in pressure provides the differential pressure required to open normally-closed one-way exit valve 48 and eject fluid from the chamber 10. The flow of fluid during this phase of operation is depicted by arrows E and GP in FIG. 5 of the drawings.

The user then increases the volume of his or her mouth cavity to withdraw the same air previously used to inflate the barrier 24. This is shown in FIG. 6 of the drawings where the deflation of the impregnable barrier 24 causes air, as represented by the arrows C, to be withdrawn from the volume or space between the elastic barrier 24 and the top closure or snap-on cap 20 and into the user's mouth. As this occurs, there is a decrease in pressure within the chamber 10 space bounded by the barrier 24, cylinder 18 and cap 22 causing normally-closed one-way valve 46 to open. This decrease in pressure or partial vacuum results in body fluid being drawn through the catheter tube 14, the now-open valve 46 and into the chamber 12. This action can best be seen in FIG. 6 of the drawings by arrows labeled C and LP. The gas and vapor component of body fluid are ejected via the exit tube 38 and one-way tip 48 when the user again decreases the volume of his or her mouth cavity.

Possible rupture of the barrier 24 is prevented when the barrier 24 comes into contact with the open end of the exit tube 38. The back pressure that builds up in the space bounded by barrier 24, cylinder 18 and bottom closure 22 balances the combined forces of barrier 24 resilience and pressure in the space bounded by barrier 24 and top closure 20 making further inflation by the human-mouth impossible. The resilience of the elastic barrier 24 also assists the pumping source in the withdrawal of fluid from a body cavity, as will also be appreciatead.

Figure 13:
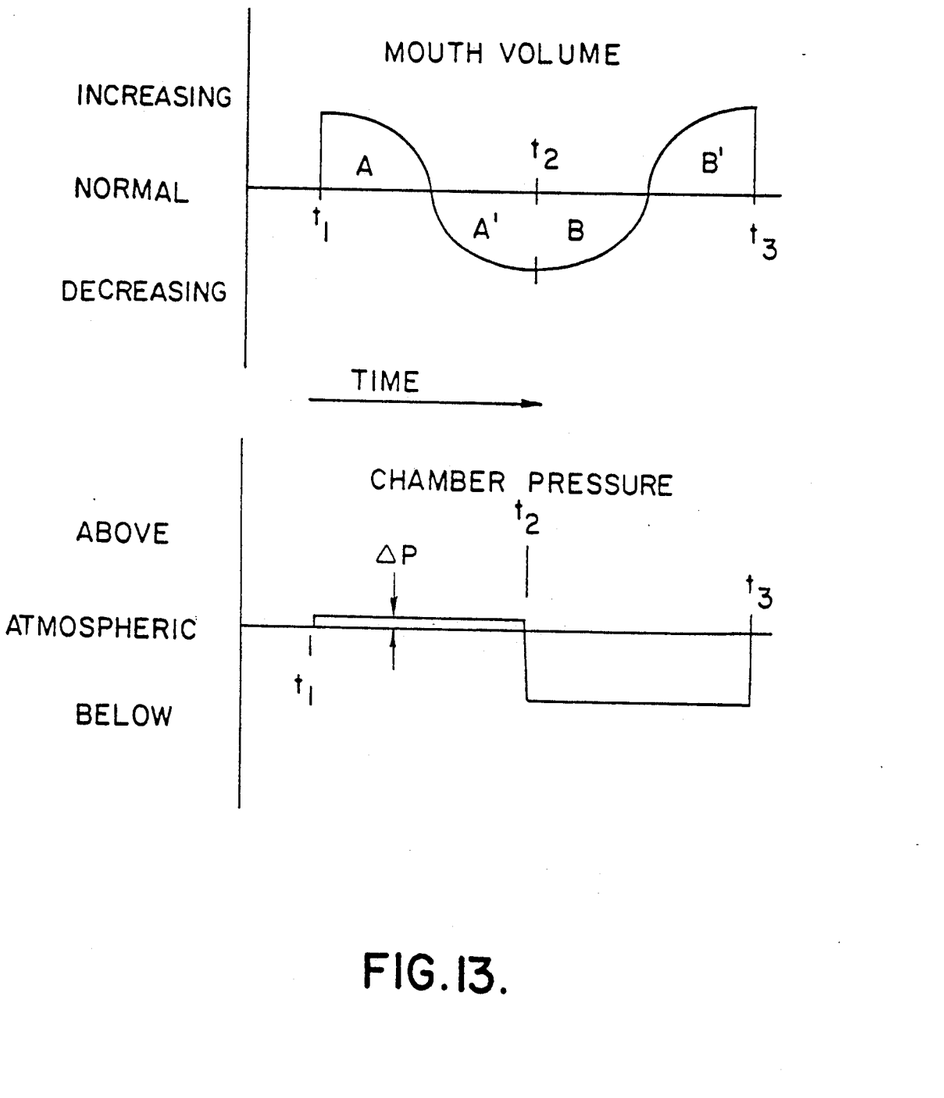
FIG. 13 shows the mouth volume and chamber pressure distribution as the user forces air into and draws air from the aspirator device.

The inner workings of the aspirator may better be described with reference to FIGS. 1,3, and 13 of the drawings. FIG. 13 shows mouth volume in the upper graphical plot and pressure inside the chamber 12 of FIGS. 1 and 3, in the lower graphical plot. Both plots in FIG. 13 are drawn to the same time scale. The plots in FIG. 13 are hypothetical and in practice will not be symmetrical smooth curves as shown.

The user increases the volume of his or her mouth cavity and then seals his or her lips about the mouthpiece 40 and decreases the volume of his or her mouth cavity causing air to be expelled from the mouth through the mouthpiece 40 and tube 16 and into the space bounded by barrier 24 and top closure 20 thus inflating the barrier 24.

In FIG. 13, the sum of areas A and A' represent the total volume of air from the user's mouth inflating the barrier 24. The total volume of air withdrawn from the barrier 24 is represented by the sum of areas B and B'.

The pressure in the space bounded by the barrier 24, the cylinder 18 and the lower closure 22 is shown in the lower plot in FIG. 13. The pressure throughout the inflating of barrier 24 occurs throughout time period t1 to t2 and is marked P. The pressure P is very low, a few mm of H2O, and is that pressure required to open normally-closed one-way valve 48 and to force gas and vapor and any excess fluid from the chamber 10 through the exit tube 38 and valve 48 against atmospheric pressure to the outside.

The portion of the plot from t2 to t3, in the lower plot of FIG. 13, represents the partial vacuum needed to cause fluid to flow from the body cavity, a region of higher pressure, through the catheter tube 14 and one-way valve 46 into the chamber 12, a region of lower pressure. The time t1 to t2 is determined primarily by the user of the aspirator. The time period t2 to t3 is dependant on the suction provided by the user, the resilience of the barrier 24 in attempting to regain it unflated shape, the viscosity of the body fluid being drawn through the catheter tube 14 and the diameter and length of the catheter tube 14. If the catheter 14 becomes clogged, or the body fluid is unusually thick, or the user wishes to accelerate flow, he or she sucks harder on the mouthpiece 40.

It is noted that the length to diameter ratio of the barrier 24 is between 1 and 2 when fully inflated and that it is inserted only a short distance into the cylinder 18 during assembly as can be seen in FIG. 3. It is further noted that it was found through experimentation that a certain amount of restoring resilience of the barrier 24 improved the performance of the aspirator device particularly when repeated cycles of inflation-deflation of the barrier are necessary to remove body fluids. Condoms were found to possess features needed for the barrier 24 and were used in experimental and prototype units.

It will be noted in FIG. 6 of the drawings that the fluid F may be easily seen through the clear plastic cylinder 18 of the isolation chamber 12 for quick visibility and/or measurement. Where measurement is desired, the cylinder 18 may be provided with suitable lines to represent the amount of liquid collected, usually measured in CC's of liquid. The exit tube 38 extends for a predetermined distance upwardly into the isolation and liquid-collector chamber 12 to enable a predetermined amount of liquid F to be collected within the air-tight isolation chamber 12 below the open upper end of the exit tube 38, while also permitting any excess liquid to be exhausted through the one-way exit tube 38 and associated one-way tip or valve 48. As will be appreciated, when the liquid F extends above the open upper end of the one-way exit tube 38, excess liquid will be exhausted much in the same way as gas and vapor represented by the arrows GP in FIG. 5 of the drawings.

FIGS. 7-9 show the combination isolation and fluid-collection chamber 12 at various attitudes or orientations, in order to illustrate that the aspirator device 10 is insensitive to orientation. Thus, in FIG. 7 of drawings, the normal and typical orientation is shown, such as that described in connection with FIGS. 4-6 of the drawings. In FIG. 8, the combination isolation and liquid-collector chamber 12 has been tilted or tipped to a horizontal orientation, with the liquid F drawn by gravity along the lower internal cylindrical wall of the cylinder 18. In this instance, the aspirator device 10 will function in the same manner as before, except that the liquid F will be relieved through the exit tube 38 when the liquid reaches the open inner end of exit tube 38. In FIG. 9, when the isolation and liquid-collector chamber 12 has an upside-down or inverted position, the liquid F will begin to fill up the space between barrier 24 and the lower closure or snap-on cap 22, shown at an upper inverted position in FIG. 9 of the drawings. When the impregnable barrier 24 is expanded or contracted, the fluid F will be displaced; however, in all other respects, the aspirator device 10 will function as before. In the same way, excess liquid F is evacuated through the exit tube 38 and associated one-way tip or valve 48 when the liquid F reaches the open inner end of the exit tube 38.

Unlike prior art devices which may cause fluid to be drawn into the user's mouth when operated from a position other than that shown in FIG. 7, the aspirator device 10 of the present invention can be used in various attitudes or orientations, as shown in FIGS. 7-9, for example, without changing the function or operation of the device, and without causing fluid to come into contact with the user's mouth.

Figure 14:
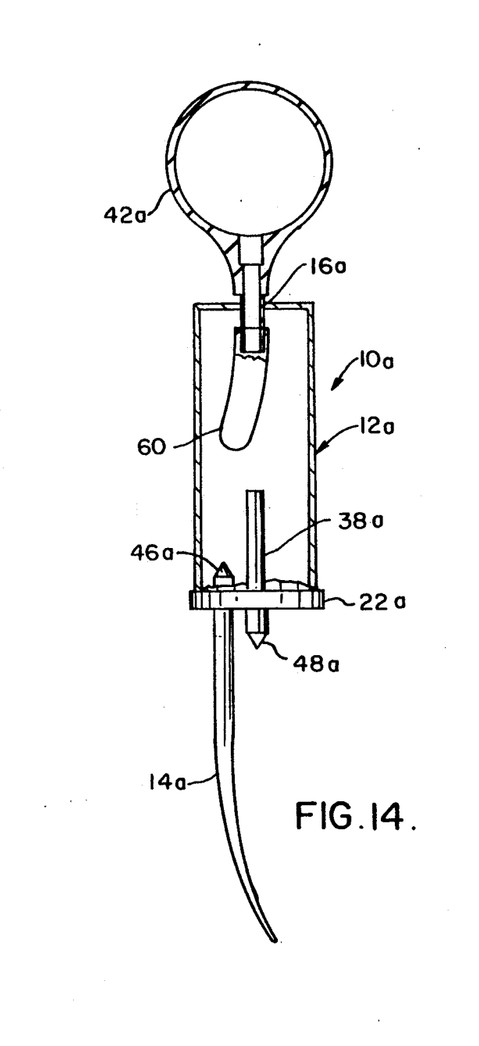
FIG. 14 is a sectional view of a modified hand operated aspirator device with included balloon barrier, in an at-rest position.
Figure 15:
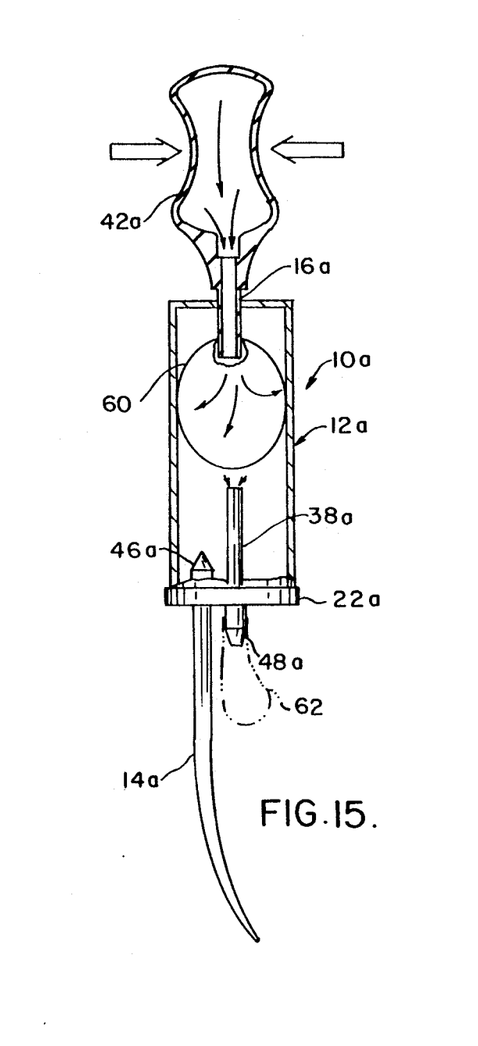
FIG. 15 is a sectional view of the modified hand-operated aspirator device shown in FIG. 14 during collapse of the squeeze bulb and consequent expansion of the balloon barrier.
Figure 16:
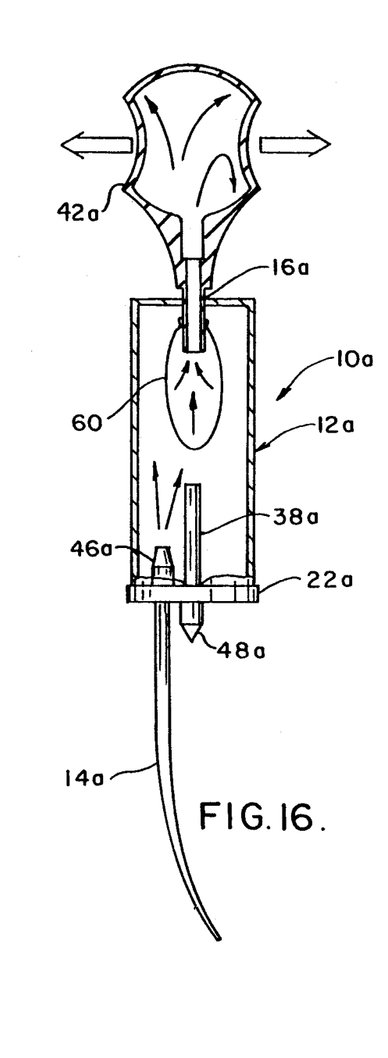
FIG. 16 is a sectional view of the modified hand-operated aspirator device shown in FIG. 14 during release and expansion of the squeeze bulb and consequent contraction of the balloon barrier.

Reference is now made to the embodiment shown in FIGS. 14-16 wherein like parts are represented by the same numeral as the FIGS. 1 and 3-3 embodiment with the suffix "a" being added to designate like parts. In this embodiment, a hand-operated aspirator 10a is shown with the squeeze bulb 42a being attached to the upper end of a short pump tube 16a that extends through an upper wall of the combined isolation and liquid-collection chamber 12a. As shown in FIGS. 14-16, the squeeze bulb 42a is immediately above the chamber 12a, although it could be positioned a substantial distance from the chamber 12a, as shown in FIG. 2, if desired.

Attached to the lower end of the pump tube 16a is an elastic balloon barrier or booster 60 which is mounted to the pump tube 16a as illustrated. The balloon barrier or booster 60 operates in much the same way as the elastic barrier or booster 24, although as will be appreciated, the balloon barrier or booster 60 has a different configuration than the barrier 24, so as to inflate and deflate in the form shown in FIGS. 15-16, as compared with FIGS. 5-6 barrier 60 inflation and deflation. The purpose; however, is the same in providing an inflatable/deflatable barrier that expands or contracts in response to changes in air volume from the air source to remove body fluids from a body cavity, while separating the user from contact with such body fluids.

In addition, the balloon barrier or booster 60 in the FIGS. 14-16 embodiment may be capable of quickly expanding from a very small to a large shape, while contracting in the same manner, as shown in FIGS. 15-16 of the drawings. In its at rest position, the balloon barrier or booster 60 is shown in FIG. 14 as occupying a very small space. When the squeeze bulb 42a is squeezed; however, as shown in FIG. 15 of the drawing, air is forced into the balloon barrier or booster 60 which then expands to decrease the volume of air in the large space of the chamber, (outside of the balloon barrier or booster 60). This forces gas and excess liquid, if any, out through the vent or exit tube 38a, as the one-way valve 48a opens for this purpose. When the squeeze bulb 42a is released, to withdraw air previously forced into the balloon barrier or booster 60, the balloon barrier or booster 60 will contract and create a partial vacuum in the large space of the chamber 12a, (outside of the balloon barrier or booster 60). This partial vacuum will open the one-way valve 46a, as shown in FIG. 16, to draw gas and fluids from the body cavity through the first elongated tube 14a, into the chamber 12a.

It is further noted that the partial vacuum created by the bulb 42a is augmented or "boosted" by the resilience of the balloon 60 to provide an aspirator having suction greater than can be provided by the bulb 42a alone. This feature is most useful in cases where fluids drawn are highly viscous or sticky.

It will also be appreciated that the elastic balloon barrier or booster 60 may be used with either a mouth-operated aspirator device or hand-operated aspirator device, as desired.

Note finally in FIG. 15 of the drawings that a storage balloon or container 62 is shown mounted to the lower end of the exit tube 38a above the one-way valve tip 48a for receiving overflow products discharged from the chamber 12a. The storage chamber can be expandable, as in the case of a balloon, or may simply comprise a storage bag. In either case, the overflow products discharged from the chamber 12a are conveniently collected in the storage chamber for disposal, along with the aspirator 10a. The storage balloon or container 62 may also be used with the FIGS. 1-13 embodiment, if desired.

From the foregoing, it will now be appreciated that the mouth-operated aspirator device, as well as the hand-operated aspirator device, of the present invention provides new and important features and advantages which are totally absent from prior art designs, and which also increases the safety, efficiency and operation of aspirator devices. The elastic barrier 24 or 60 has numerous advantages including the prevention of gas, vapor and/or liquids from entering into the user's mouth via the combination isolation and liquid collection chamber 12. At the same time, it prevents the user from forcing gas or vapors from the user's mouth into a newborn infant, in the mouth-operated aspirator device. The elastic barrier also serves as pressure transfer medium for the pumping action required within the isolation and liquid-collector chamber 12. The simplicity and low cost of the elastic barrier or booster 24 or 60 and one-way tips or valves 46 and 48, and other related components, provides an aspirator device which overcomes all of the aforenoted deficiencies, while retaining all of the advantages of prior art devices. Thus, the benefit to cost ratio is exceptionally attractive.

In view of the above, it will be seen that the several objectives of the invention are achieved and other advantageous results are obtained.

As various changes could be made in the above constructions and methods without departing from the scope of the invention, it is intended that all matter contained in the above description or shown in the accompanying drawings shall be interpreted as illustrative and not in a limiting sense.

We claim:

1. An aspirator device for removing body fluids comprising an air-tight chamber for receiving body fluids, first and second elongated tubes having first and second sealed passageways communicating with said air-tight chamber and a one-way exit tube operably associated with said air-tight chamber, the first elongated tube having a free end adapted to be inserted into a body cavity for fluid communication with body fluids, the second elongated tube having a free end to which an air source is operably connected, an inflatable/deflatable elastic barrier operably associated with said second elongated tube in order to allow said air source to first inflate and thereby expand the elastic barrier and force an equal volume of air through said one-way exit tube and from said air-tight chamber, said elastic barrier also being contracted when said air source deflates to open a one-way valve associated with said first elongated tube, in order to draw body fluid through the first sealed passageway of the first elongated tube for deposit of liquid content in the air-tight chamber of the liquid collector and subsequent ejection of gas and vapor content when said elastic barrier is again inflated, and said one-way exit tube extending a predetermined distance within said air-tight chamber to an open upper end to enable a predetermined amount of liquid to be collected within said air-tight chamber below the open upper end of said one-way exit tube, while permitting gas and vapor and any excess liquid to be exhausted through the one-way exit tube.

2. The aspirator device as defined in claim 1 wherein said elastic barrier extends substantially across the air tight chamber adjacent to and being operably associated with said second elongated tube.

3. The aspirator device as defined in claim 1 wherein said elastic barrier comprises a balloon barrier connected to a lower end of said second elongated tube within said air-tight chamber.

4. The aspirator device as defined in claim 1 wherein a mouthpiece is attached to the free end of said second elongated tube enabling a user's mouth to provide the air source used to increases or reduces the volume of air applied causing inflation or deflation of said elastic barrier.

5. The aspirator device as defined in claim 1 wherein said air source comprises a squeeze bulb attached to the free end of said second elongated tube.

6. The aspirator device as defined in claim 5 wherein said squeeze bulb is attached to the free end of the second elongated tube immediately adjacent to the air-tight chamber.

7. The aspirator device as defined in claim 1 wherein said one-way exit tube includes a normally-closed one-way valve extending outside of said air-tight chamber.

8. The aspirator device as defined in claim 7 wherein said exit tube comprises a one-way tip attached to the lower end of said exit tube, said one-way tip including a normally-closed one-way valve which opens and closes in response to inflation and deflation of said elastic barrier.

9. The aspirator device as defined in claim 8 wherein an exit tube extends a predetermined distance into the air tight chamber to contact the elastic barrier when fully inflated and thereby prevent further inflation and possible rupture.

10. The aspirator device as defined in claim 9 wherein the normally-closed one-way valve associated with said first elongated tube is mounted within said air-tight chamber.

11. The aspirator device as defined in claim 10 wherein said one-way valve associated with said first elongated tube also includes a normally-closed one-way tip that opens in response to removing air from and thereby deflating said elastic barrier.

12. The aspirator device as defined in claim 11 wherein said fluid collector includes an upper transverse opening, said elastic barrier being positioned across said upper transverse opening, a top closure for overlying and closing said upper transverse opening, and said closure having a through opening for receiving said second elongated tube therein.

13. The aspirator device as defined in claim 12 wherein said fluid collector also includes a lower transverse opening, a bottom closure for overlying and closing said lower transverse opening, and through openings in said bottom closure for receiving said one-way exit tube and said first elongated tube therethrough.

14. In an aspirator device for removing body fluids including a fluid collector having an air-tight chamber for receiving body fluids, first and second elongated tubes having first and second sealed passageways communicating with said air-tight chamber, said first elongated tube having a free end adapted to be inserted in a body cavity for fluid communication with body fluids, said second elongated tube having a free end for connection to an air source to establish a partial vacuum in said passageways to remove fluids from said body for deposit of liquid content in said fluid collector, the improvement comprising an elastic barrier to separate said first and second sealed passageways from each other while allowing differential air pressure from the air source to inflate and deflate and thereby expand or contract the elastic barrier for ejecting gas, vapor and excess liquid from or drawing body fluid into said air-tight chamber, and a one-way exit tube for exhausting an equal volume of air filling said air-tight chamber on one side of said elastic barrier during expansion thereof, said one-way exit tube being closed during contraction of said elastic barrier to establish a vacuum within said second sealed passageway for removing fluids from the body cavity for deposit in said fluid collector, said one-way exit tube extending for a predetermined distance within said air-tight chamber and terminating in an open upper end to enable a predetermined amount of liquid to be collected within said air-tight chamber below said open upper end, while permitting any excess liquid to be exhausted through the one-way exit tube.

15. The improvement as defined in claim 14 wherein the first elongated tube which is inserted into the body cavity, includes a one-way valve mounted within said air-tight chamber which is opened in response to contraction of said elastic barrier.

16. The improvement as defined in claim 15 wherein said one-way exit tube includes a normally-closed one-way valve outside of said air-tight chamber while the normally-closed one-way valve of said first elongated tube is within said air-tight chamber, both of said one-way valves comprising one-way tips which are responsive to differential air pressure.

17. An aspirator device for removing body fluids comprising:

a rigid air-tight chamber for receiving body fluids wherein the volumetric-space inside said chamber is divided into a small space and a large space by an inflatable/deflatable elastic barrier, a first elongated tube having a sealed passageway with one end heretically sealed to said chamber for one-way fluid communication with the large space in said chamber, the free end of said first elongated tube adapted for insertion into a body cavity, a second elongated tube having a sealed passageway with one end hermetically sealed to said chamber for two-way air communication with the smaller space in said chamber, the free end of said second elongated tube being connected to an air-pumping source, and a one way exit tube having a sealed passageway and being hermetically sealed to said chamber and extending a predetermined distance to an open upper end in the larger space of said chamber sufficient to permit body liquids to be collected in said larger space below the open upper end of said exit tube, the other end of said exit tube extending outside said chamber.

18. The aspirator as defined in claim 17 wherein said elastic barrier extends substantially across the air tight chamber adjacent to said second elongated tube and defining the smaller space therein, the larger space extending on the opposite side of said elastic barrier within said air-tight chamber.

19. The aspirator as defined in claim 17 wherein said elastic barrier comprises a balloon barrier connected to a lower end of said second elongated tube within said air-tight chamber, the smaller space being within said balloon barrier while the larger space extends outside of said balloon barrier.

20. The aspirator as defined in claim 17 and including a storage container positioned over a one-way valve tip at the other end of the exit tube for receiving products discharged from the chamber.

* * * * *